United States Patent
Inoue et al.

(10) Patent No.: US 7,435,321 B2
(45) Date of Patent: Oct. 14, 2008

(54) PROTON CONDUCTOR GAS SENSOR

(75) Inventors: Tomohiro Inoue, Kawabe-gun (JP);
Hideki Okoshi, Toyonaka (JP); Takeshi Nakahara, Minoo (JP); Kazunari Kaneyasu, Toyonaka (JP)

(73) Assignee: Figaro Engineering Inc., Osaka (JP)

( * ) Notice: Subject to any disclaimer, the term of this patent is extended or adjusted under 35 U.S.C. 154(b) by 781 days.

(21) Appl. No.: 10/476,947

(22) PCT Filed: May 23, 2002

(86) PCT No.: PCT/JP02/05027

§ 371 (c)(1),
(2), (4) Date: Nov. 6, 2003

(87) PCT Pub. No.: WO02/097420

PCT Pub. Date: Dec. 5, 2002

(65) Prior Publication Data

US 2004/0134780 A1 Jul. 15, 2004

(30) Foreign Application Priority Data

May 25, 2001 (JP) ............................ 2001-157167

(51) Int. Cl.
*G01N 27/407* (2006.01)
(52) U.S. Cl. ....................... 204/424; 204/431
(58) Field of Classification Search ................ 204/424, 204/410, 431, 432; 205/784
See application file for complete search history.

(56) References Cited

U.S. PATENT DOCUMENTS

| 4,227,984 | A | 10/1980 | Dempsey et al. |
| 4,820,386 | A | 4/1989 | LaConti et al. |
| 5,527,446 | A | 6/1996 | Kosek et al. |
| 5,650,054 | A | 7/1997 | Shen et al. |
| 6,016,683 | A | 1/2000 | Betts et al. |
| 6,404,205 | B1 * | 6/2002 | Kitamura ................. 324/464 |

FOREIGN PATENT DOCUMENTS

| EP | 0 114 667 A | 8/1984 |
| EP | 0 710 835 A | 5/1996 |
| EP | 0 990 895 A | 4/2000 |
| WO | WO 01 14864 A | 3/2001 |

OTHER PUBLICATIONS

Heqing, Yan et al, "A Solid Polymer Electrolyte-Based Electrochemical Carbon Monoxide Sensor", Sensors and Actuators B, Elsevier Sequoia S.A., Lausanne, CH, vol. B17, No. 2, 1994, pp. 165-168.

* cited by examiner

*Primary Examiner*—Kaj K Olsen
(74) *Attorney, Agent, or Firm*—Rothwell, Figg, Ernst & Manbeck, P.C.

(57) ABSTRACT

A MEA 6 having a proton conductive membrane is sandwiched by metal plates 14, 15 and they are further sandwiched by heat pressable films 20, 21. An opening 24 and an opening 18 are formed in the heat pressable film 20 and the metal plate 14, respectively so that an electrode 10 is used as the sensing electrode and exposed to atmosphere to be measured. Openings 25, 19 are formed in the heat pressable film 21 and metal plate 15, respectively so that an electrode 11 is used as the counter electrode, and water vapor is supplied to the electrode from a water pack.

11 Claims, 16 Drawing Sheets

F I G. 1
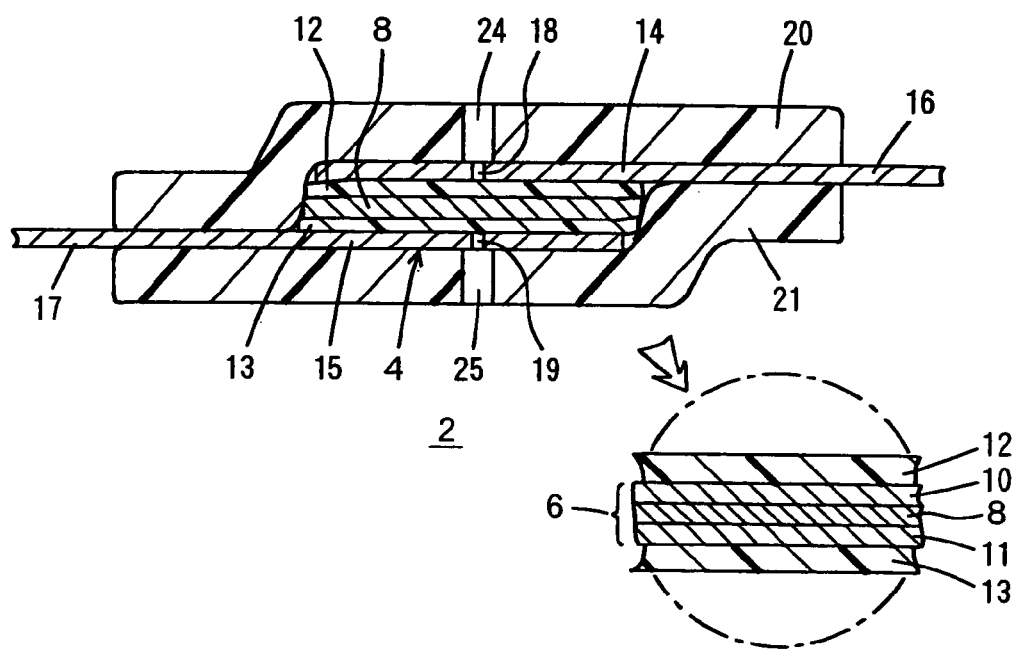

F I G. 8
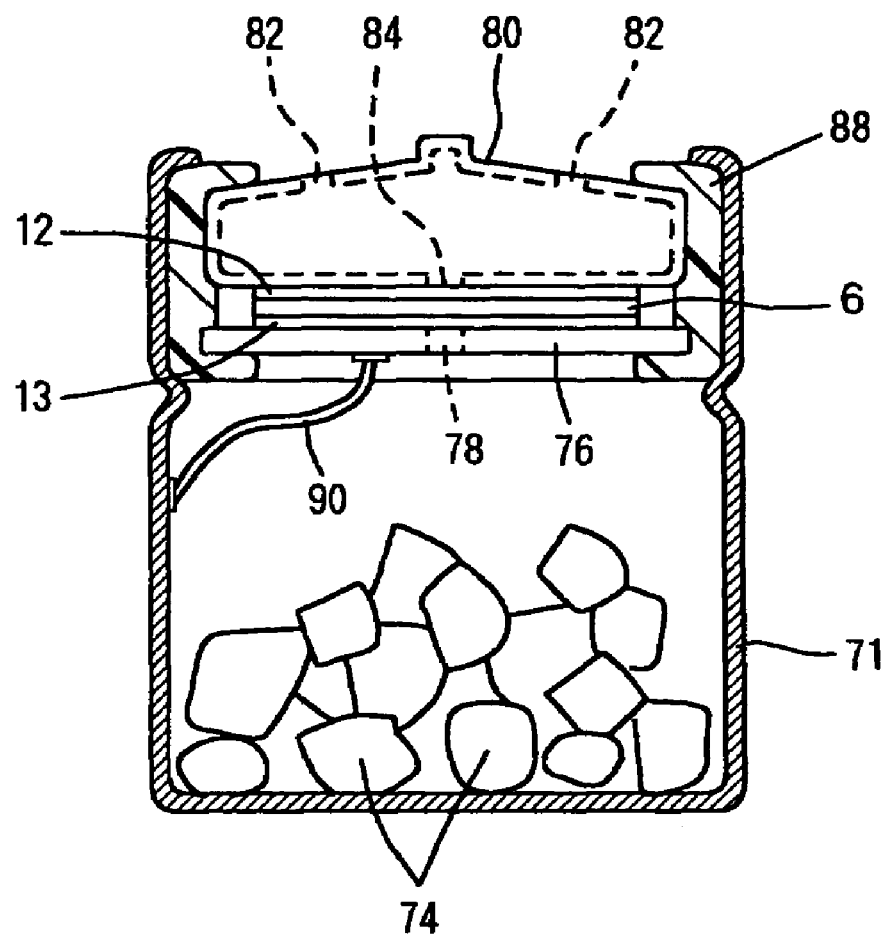

F I G. 2 1
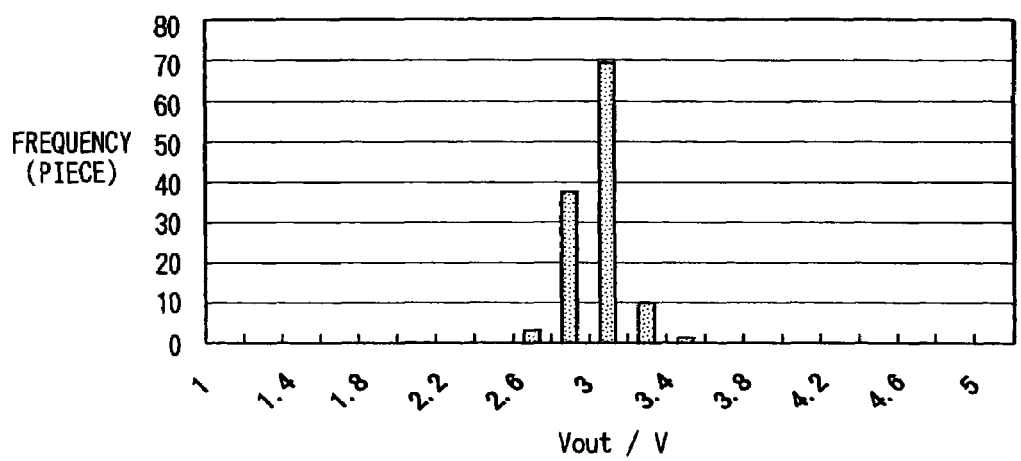
F I G. 2 2
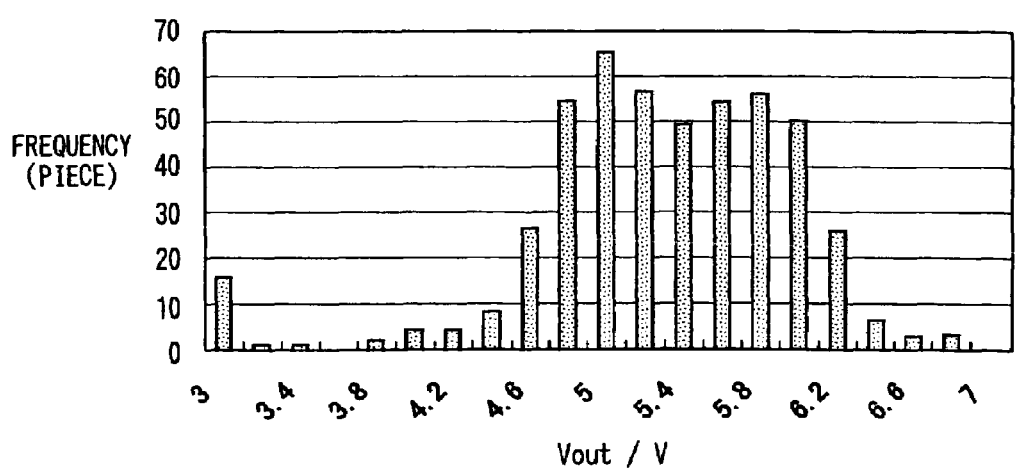

PROTON CONDUCTOR GAS SENSOR

CROSS REFERENCE TO RELATED APPLICATION

This application is a 35 USC § 371 National Phase Entry Application from PCT/JP02/05027, filed May 23, 2002, and designating the U.S.

1. Technical Field

The present invention relates to proton conductor gas sensor, and particularly relates to its assembly.

2. Background Art

A proton conductor gas sensor using metal can construction is known (U.S. Pat. No. 5,650,054). Its sensing element is formed by sandwiching a polymer electrolyte membrane (PEM) of an organic synthetic resin between a pair of electrode membranes to produce a membrane electrode assembly (MEA) and then sandwiching the MEA between carbon sheets or the like. Water is contained in a metal can, a first metal washer is arranged above the water, and the sensing element is placed on the metal washer. Another face of the sensing element is covered by a second metal washer, and the second washer and the sensing element are pressed towards the first washer by an insulating elastic member (U.S. Pat. No. 5,650,054). The second washer serves as the terminal of the sensing electrode side of the sensor, and the metal can, which is electrically continuous to the first washer, serves as the terminal of the counter electrode side. The continuity between the MEA and the washers are secured by the pressing of the elastic member. The configuration of such a gas sensor, however, is limited to configurations that are similar to those of batteries.

3. Disclosure of the Invention

A primary object of the present invention is to provide a new assembly or assembled structure of proton conductor gas sensor, and in particular, to easily connect the sensing electrode and the counter electrode to leads, reduce overshoots and undershoots of the sensor output, and reduce the dispersion of the sensor outputs.

A secondary object of the present invention is to prevent poisoning of the sensing electrode.

An additional object of the present invention is to attach a flexible water pack.

Another secondary object of the present invention is to prevent molds from growing in the water contained in the water pack.

Another additional object of the present invention is to control evaporation of the water from the flexible water pack.

Another additional object of the present invention is to prevent any damages to the sensor unit.

Another additional object of the present invention is to enable supplementation of the water contained in the container.

Another additional object of the present invention is to prevent the water from surging inside the container.

The proton conductor gas sensor according to the present invention has a sensor unit comprising a sensing element comprising a proton conductive membrane; a membranal sensing electrode and a membranal counter electrode, which are separated from each other and attached at least on one face of the proton conductive membrane; a first metal plate that covers the sensing electrode and is provided with an opening and a lead part; and a second metal plate that covers the counter electrode and is provided with a lead part, and a first synthetic resin film and a second synthetic resin film, which sandwich the sensing element between themselves and are greater in size than any of the proton conductive membrane, sensing electrode, counter electrode, first and second metal plates, wherein the first and second synthetic resin films are bonded together, and by that, the first metal plate is pressed towards the sensing electrode side and the second metal plate is pressed towards the counter electrode side, and an electric contact between the first metal plate and the sensing electrode and an electric contact between the second metal plate and the counter electrode are secured, and wherein the respective lead parts protrude out of points between the first and second synthetic resin films.

Preferably, the first synthetic resin film is provided on a side at which the first synthetic resin film covers the first metal plate, and a filter for removing poisoning substances is provided between the first metal plate and the first synthetic resin film or outside the first synthetic resin film.

Preferably, the first synthetic resin film is provided on a side at which the first synthetic resin film covers the first metal plate, the sensor unit is mounted on a flexible pack, which is covered by an airtight film and holds water in a condensed phase, on the side of the second synthetic resin, and the flexible pack is provided with a part from which the airtight film is removed, and the part from which the film is removed is connected to the second synthetic resin film.

Preferably, the second synthetic resin film is provided with an opening, and the opening in the second synthetic resin film is connected to the part from which the film is removed.

Preferably, the water in a condensed phase is made to contain an antiseptic.

Particularly preferably, the flexible pack comprises at least two layers of synthetic resin films and an airtight ceramic film that is sandwiched between the two layers.

Preferably, the sensor unit is mounted inside the flexible pack.

Preferably, further, a third metal plate, which is thinner than the first metal plate, is connected to the opening in the first metal plate, and is provided with an opening being smaller in diameter than that in the first metal plate, is provided.

Preferably, the first synthetic resin film is provided on a side at which the first synthetic resin film covers the first metal plate, and the sensor unit is mounted on a water container of a synthetic resin on the side of the second synthetic resin film.

Preferably, the second synthetic resin film is provided with an opening that is connected to the atmosphere in the water container.

Particularly preferably, the water container comprises a synthetic resin bottle, a synthetic resin cap being airtightly screwed on the bottle and having an opening in a point opposite to the bottle, and water in a condensed phase being contained in the bottle, and the sensor unit is mounted on the cap in the opposite position.

Preferably, the sensor unit is mounted inside the cap at the opposite position.

Preferably, the water in a condensed phase is contained in a watertight and water vapor permeable inner bag, and the inner bag is contained in the water container.

In the present invention, as the first synthetic resin film and the second synthetic resin film are bonded together, these films exert forces, which press the first and second metal plates towards the sensing electrode side and the counter electrode side. As a result, an electric path is formed from the sensing electrode, via the first metal plate, to the lead part, and similarly, an electric path is formed from the counter electrode, via the second metal plate, to the lead part.

The sensing electrode has to be connected to the atmosphere to be measured, and the counter electrode has to be connected to a different atmosphere. To this end, for example, the sizes of the first and second metal plates, diameters of the openings in these plates, the air permeability of the first and second synthetic resin films and diameters of openings in these films, and a container of water can be utilized. For example, an opening may be made in only the first metal plate while no opening is made in the second metal plate. Or the counter electrode may be connected to a container holding water so as to isolate the counter electrode from the atmosphere to be measured.

The present inventor found that when the atmosphere of the sensing electrode side bypasses to the counter electrode side, overshoots and/or undershoots will be generated in the sensor output. In this case, as there is a resistance against air transmission by, for example, the proton conductive membrane between the sensing electrode and the counter electrode, the atmosphere of the counter electrode will follow the atmosphere of the sensing electrode with a lag. When a gas to be measured, for example, CO is introduced to the sensing electrode side, at first, a large output will be obtained because there is no CO on the counter electrode side. However, as CO bypasses to the counter electrode side with time, the difference in CO concentration between the sensing electrode and the counter electrode will decrease, and in turn, the output will decrease. As a result, an overshoot will be generated. On the other hand, when CO is removed from the sensing electrode side, due to a time lag until the CO on the counter electrode side is removed, an undershoot will be generated. In the present invention, the sensing element comprising the proton conductive membrane, sensing electrode, counter electrode, first and second metal plates is sandwiched between a pair of synthetic resin films, and these synthetic resin films are bonded together. When, for example, the sides of the proton conductor membrane are sealed by the first and second synthetic resin films, or when sealing members such as O-ring are arranged on the sides of the proton conductive membrane, overshoots and undershoots of the sensor output can be eliminated mostly with ease.

As described above, according to the present invention, the structure of the gas sensor can be simplified, and leads can be easily connected to the sensing electrode and counter electrode. Moreover, the overshoots and undershoots of the sensor output can be reduced. Furthermore, the first and second metal plates can be positioned moderately. For example, when the sensing element is sandwiched between the first and second synthetic resin films and the assembly is heat-pressed, the whole procedure is free of any process that disturb the positions of the sensing electrode and the counter electrode in relation to the first and second metal plates. Hence dispersion of the positions of metal plates in relation to the sensing electrode and the counter electrode can be reduced, and in turn, dispersion of the sensor output can be reduced.

When a filter of active carbon, silica gel, zeolite, etc. is used to remove poisoning substances, poisoning of the sensing electrode can be prevented.

When water is retained in a flexible pack, a new structure of a reservoir of water for moistening the proton conductive membrane is obtained.

When an antiseptic is added to the water in the flexible pack, mold growth can be prevented, and in turn, clogging, by molds, of the opening in the second metal plate on the counter electrode side and contamination of the counter electrode can be prevented.

When the flexible pack comprises at least two layers of synthetic resin films and an airtight ceramic film being sandwiched between the two layers, water in the flexible pack can be prevented from evaporation out of the pack. When a metal film is layered on a synthetic resin film to ensure airtightness, the edges of the metal film will be exposed and oxidized at a position which the metal film is removed to connect to the sensor unit, and water evaporation at the position will be quickened. In contrast to this, when an airtight film is a film which is made by vapor deposition of silica, alumina, etc., even if the edges of the film are exposed to water, they will not deteriorate. Thus water evaporation can be controlled. This will extends the life of the sensor.

The sensor unit can be mounted inside a flexible pack. With this arrangement, in contrast to a case wherein the sensor unit is exposed out of the pack, the sensor unit can be protected by the pack.

When the sensor unit is used under diffusion control condition, the sensor output is proportional to the rate of gas supply to the sensing electrode. The opening of the first metal plate regulates this gas supply rate, but the first metal plate having a lead part requires a certain thickness and a certain strength. Hence it is difficult to work on the plate to obtain accurate opening diameters. In contrast to this, it is easy to provide a third metal plate, which is thinner than the first metal plate, and make a hole of accurate diameter. As a result, dispersion of the sensor output can be reduced.

The container for water is not limited to a flexible pack. Synthetic resin containers in the form of bottle or cylinder can be used. It is easy to use a bottle-shaped container and airtightly screw a cap on the bottle. When a sensor unit is mounted on the top end (the side opposite to the bottle) of the cap, the cap can be removed from the bottle to replenish or replace the water in the bottle. Then the life of the sensor can be extended.

When the sensor unit is mounted on the inner side of the cap (the side facing the bottle), the sensor unit can be prevented from damages in transport or in service.

Moreover, when water is contained in a water vapor permeable inner bag, the water can be prevented from moving around inside the water container. Surging of water may pose problems such as leakage of water and penetration of water into the sensor unit.

BRIEF DESCRIPTION OF THE DRAWINGS

FIG. 1 is a sectional view of a part of the sensor unit of an embodiment of the present invention.

FIG. 8 is a sectional view of the gas sensor of an example for comparison.

FIG. 21 is a characteristic diagram showing the distribution of the sensor output of the best embodiment at 1000 ppm of CO.

FIG. 22 is a characteristic diagram showing the distribution of the sensor output of the example for comparison of FIG. 23 at 1000 ppm of CO.

EMBODIMENTS

Figure 2:
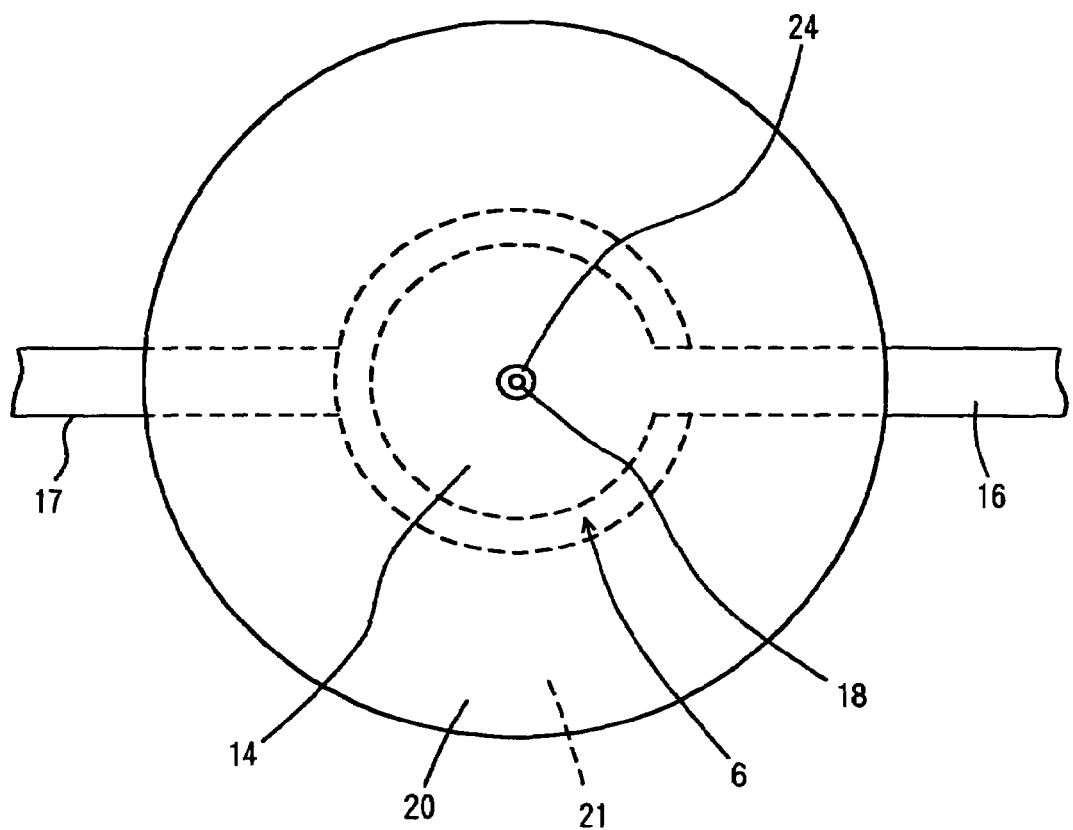
FIG. 2 is a plan view of the part of the sensor unit of the embodiment.

An embodiment of the present invention and a modification thereof are shown in FIG. 1 through FIG. 7. In FIG. 1 through FIG. 4, 2 denotes a sensor unit, 4 a sensing element, 6 a membrane electrode assembly (MEA), and 8 its polymer electrolyte membrane (PEM). 10 denotes a sensing electrode, 11 a counter electrode, and 12 and 13 porous carbon sheets having open pore 14 and 15 denote metal plates in the form of a disk, for example, a circular disk. The metal plate 14 is made to contact the sensing electrode 10 side, the metal plate 15 is made to contact the counter electrode 11 side, and 16 and 17 denote their lead parts. The metal plate 14 is provided with an opening 18, and the metal plate 15 is provided with an opening 19. However, the opening 19 in the metal plate 15 may be omitted. 20 and 21 denote heat pressable films, and 24 and 25 denote openings made in these films.

A synthetic resin film is used for the proton conductive membrane 8. Here the Gore Select membrane of Japan Gore Tex is used, and its membrane thickness is about 40 μm. Gore Select is a trade name of Japan Gore Tex. In place of the Gore Select membrane, Nafion 117 (membrane thickness: about 100 μm) of DuPont or the like may be used. The diameter of the proton conductive membrane 8 is, for example, from 5 mm to 13 mm. The sensing electrode 10 and the counter electrode 11 may be, for example, membranes having the same diameter as the proton conductive membrane 8 has. The material of these electrodes is, for example, porous membrane of Teflon in which carbon black supporting platinum or the like is dispersed. As for the carbon sheets 12, 13, for example, Torayca of Toray (Torayca is a trade name) is used.

The proton conductive membrane 8 is sandwiched between a pair of membranal electrodes to form the MEA 6. This is well known in the field of gas sensors. It is also well known that the MEA 6 is sandwiched, from above and below, between carbon sheets 12, 13 or the like. Any sheets which are electro conductive and permeable to air may be used in place of the carbon sheets 12, 13. For example, screens of metal of titanium may be used. Here, the proton conductive membrane 8, the sensing electrode 10, the counter electrode 11, and the carbon sheets 12, 13 have the same diameter. However, it may be arranged in such a way that the proton conductive membrane 8 has the largest diameter and the others have a smaller diameter.

As for the metal plates 14, 15, for example, stainless steel or nickel-plated steel or the like may be used. The thickness is about 0.1 to 0.5 mm, and the openings 18, 19 have a diameter, for example, ranging about 0.1 to 0.5 mm. The role of the openings 18, 19 is to limit the air permeability to the MEA 6. With regard to air permeability, the carbon sheets 12, 13 make the gases supplied through the openings 18, 19 diffuse in directions parallel to the faces of the metal plates 14, 15. Thus the gases are supplied to the MEA 6 over extensive areas.

The material of the heat pressable films 20, 21 are discretionary. For example, polypropylene or polyester may be used. They are made by applying heat to stick together airtightly. The film thickness is, for example, from 30 μm to 200 μm. As shown in FIG. 2, The heat pressable films 20, 21 have a diameter greater than that of the MEA 6 so that the heat pressable films 20, 21 can be heat-pressed to each other outside the MEA 6. In place of heat pressable films 20, 21, other films may be used and they may be bonded together with an adhesive instead of heat pressing.

As shown in FIG. 2, the lead parts 16, 17 protrude from the heat pressable films 20, 21 outwards and are exposed, and they are bars or plates. An opening 24 made in the heat pressable film 20 is through to the opening 18 made in the metal plate 14, and the opening 24 in the heat pressable film 20 is greater in diameter than the opening 18 made in the metal plate 14. Similarly, the opening 25 in the heat pressable sheet 21 has a diameter greater than that of the opening 119 of the metal plate 15, and the openings 19, 25 are through to each other.

When the air permeability of the heat pressable films 20, 21 is high, the openings 24, 25 may be omitted. Here, the openings 24, 25 have the same diameter, but the diameter of the opening 24 on the sensing electrode 10 side may be made smaller than that of the opening 25 on the counter electrode 11 side. Similarly, the diameter of the opening 18 may be made smaller than that of the opening 19. This is to enhance the replenishment of oxygen to the counter electrode 11 side when the sensor unit 2 is mounted on the water pack 53, which will be described later. This prevents the output from dropping at a high concentration of CO due to delayed replenishment of oxygen to the counter electrode 11.

Figure 3:
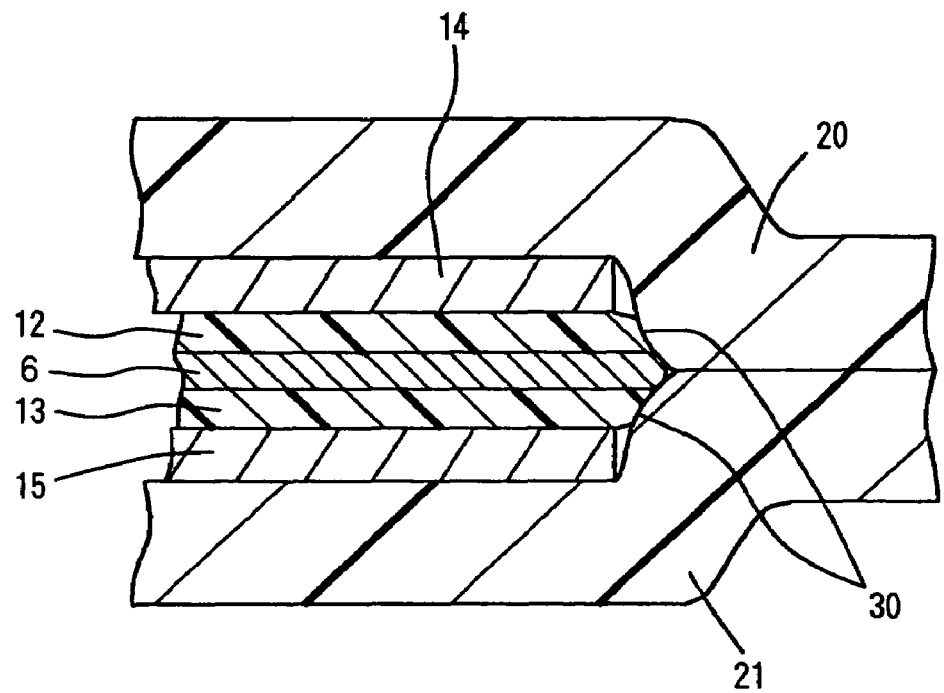
FIG. 3 is a fragmentary enlarged view of FIG. 1.

As shown in FIG. 2 and FIG. 3, it is desirable that the diameters of the metal plates 14, 15 are just a little smaller than those of the MEA 6 and carbon sheets 12, 13. With this arrangement, as shown in FIG. 3, the heat pressable films 20, 21 immediately contact with each other outside the MEA 6 and carbon sheets 12, 13 to eliminate any open space outside the MEA 6 and carbon sheets 12, 13. 30 denotes a contacting part between the heat pressable films 20, 21 and the MEA 6 and carbon sheets 12, 13.

Figure 4:
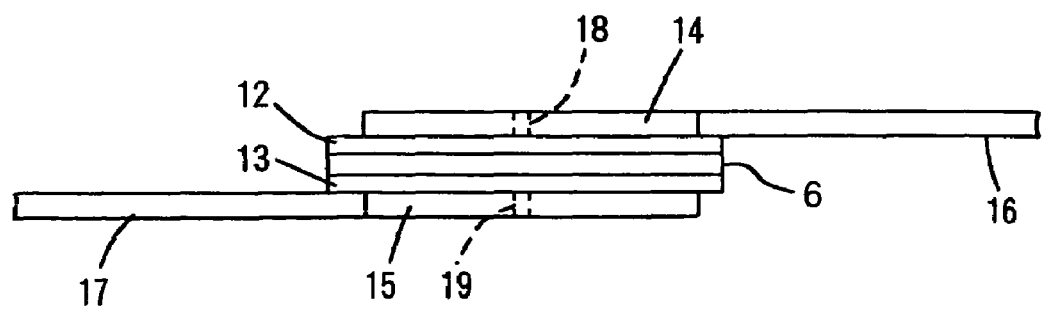
FIG. 4 is a side view of the sensing element.

FIG. 4 shows the sensor unit 2 from which the heat pressable films 20, 21 are eliminated. The carbon sheets 12, 13 are above and below the MEA 6, and the pair of metal plates 14, 15 are outside the carbon sheets 12, 13. The diameters of the metal plates 14, 15 are a little smaller than those of the MEA 6 and carbon sheets 12, 13, and the lead parts 16, 17 protrude outwards. A gas to be detected, for example CO, enters through the opening 18 on the sensing electrode 10 side into the carbon sheet 12, diffuses in the carbon sheet 12 in directions parallel to the face of the metal plate 14 and enters into the MEA 6. Then, the following reaction takes place at the interface between the sensing electrode 10 and the proton detective membrane 8 of the MEA 6:

$$CO + H_2O \rightarrow CO_2 + 2H^+ + 2e^-  \quad (1)$$

The resulting protons will diffuse through the proton conductive membrane towards the counter electrode 11 side and at the counter electrode 11 react with oxygen which is supplied through the opening 19 via the carbon sheet 13, as shown below:

$$2H^+ + 1/2 O_2 + 2e^- \rightarrow H_2O \quad (2)$$

Thus, the role of the carbon sheets 12, 13 is to ensure the use of the MEA 6 as extensively as possible so that even if the MEA 6 deteriorated partially, it would have smaller impacts on the sensor output. On the other hand, the carbon sheet 12 on the sensing electrode 10 side causes bypassing of CO or the like towards the counter electrode 11 side. The bypassing of CO towards the counter electrode 11 side starts in the open spaces outside the sides of the MEA 6 and carbon sheets 12, 13. Therefore, these parts are sealed by the heat pressable films 20, 21 to prevent bypassing of CO or the like towards the counter electrode.

In the MEA 6, the sensing electrode and the counter electrode are physically jointed to the proton conductive membrane, but the carbon sheets 12, 13 and the metal plates 14, 15 are merely arranged in their required positions. When the heat pressable films 20, 21 are mutually joined outside the sensing element 4, compressive forces are applied by the heat pressable films 20, 21 to the sensing element 4. These compressive forces press the metal plate 14 towards the carbon sheet 12 side and press the carbon sheet 12 towards the sensing electrode side. Similarly, the compressive forces will press the metal plate 15 towards the carbon sheet 13 and press the carbon sheet 13 towards the counter electrode side. As a result, the electric connection in the sensing element 4 is secured by the pressures generated by the heat pressable films 20, 21.

The roles of the openings 24, 25 made in the heat pressable films 20, 21 are to supply CO, etc. to the sensing electrode side and to supply oxygen, etc. to the counter electrode side. In the embodiment, the sensor unit 2 is used by attaching it to a water pack shown in FIG. 5 and FIG. 6. The water pack, however, may be omitted. In that case, the opening 19 and the opening 25 may be eliminated, and oxygen which is required on the counter electrode side may be supplemented by allowing oxygen to diffuse from the sensing electrode side through the MEA 6.

Figure 5:
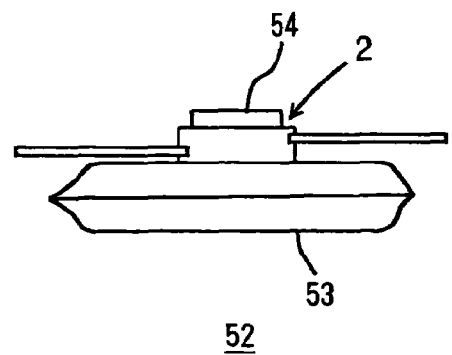
FIG. 5 is a side view showing the overall structure of the gas sensor of the embodiment.
Figure 6:
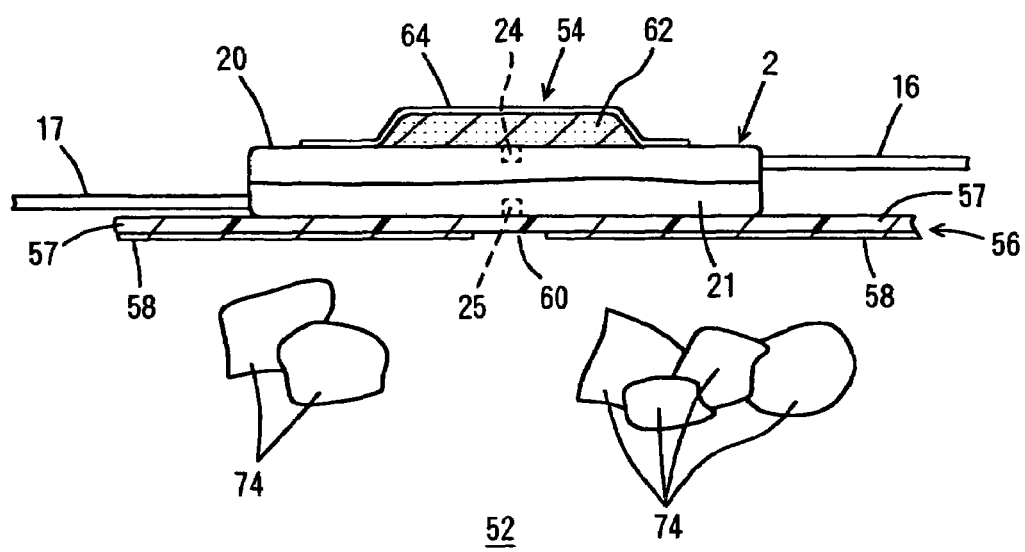
FIG. 6 is a fragmentary enlarged view of a part of FIG. 5, showing fitting of a filter and fitting of a water pack.

FIG. 5 and FIG. 6 show a gas sensor 52, to which a water pack 53 is attached. 54 denotes a filter. The water pack 53 is a pack of a film 56 wherein a water vapor permeable film 57 is layered on a moistureproof (water vapor impermeable) film 58 such as a metal film. The water pack 53 is used to contain liquid water or gelled water. The meaning of water here is not limited to pure water. It may include, for example, a mixture of water and antiseptics or the like. The moistureproof film 58 comprises a metal film or the like, and a cutting 60 is made in the film 58 to connect the cutting 60 to the opening 25 so that water vapor can diffuse through the cutting 60 to the MEA side. When, for example, the heat pressable film 21 is heatpressed onto the water vapor permeable film 57, the sensor unit 2 is fixed onto the water pack 53.

The filter 54 will be explained. Chlorine, SO2, and silicon compounds, etc. are poisoning substances to the sensing electrode and the counter electrode. In particular, poisoning of the sensing electrode poses a problem. To absorb or adsorb these poisoning substances, the filter 54 is used. 62 denotes an active carbon sheet for adsorbing poisoning substances and is attached to the heat pressable film 20 by an adhesive tape 64. A sheet of silica gel or the like may be used in place of the active carbon sheet 62. When the active carbon sheet 62 is attached by the adhesive tape 64 as shown in FIG. 6, the ambient air enters into the active carbon sheet 62 from above the paper of FIG. 6 and reaches the opening 24 in the heat pressable film 20. As long gas channels can be secured, and as air can be supplied through an extensive area rather than only a part most adjacent to the opening 24, the life of the active carbon sheet 62 can be extended. As no specific narrow channels are formed in the active carbon sheet 62, the load on the active carbon sheet 62 is reduced.

Figure 7:
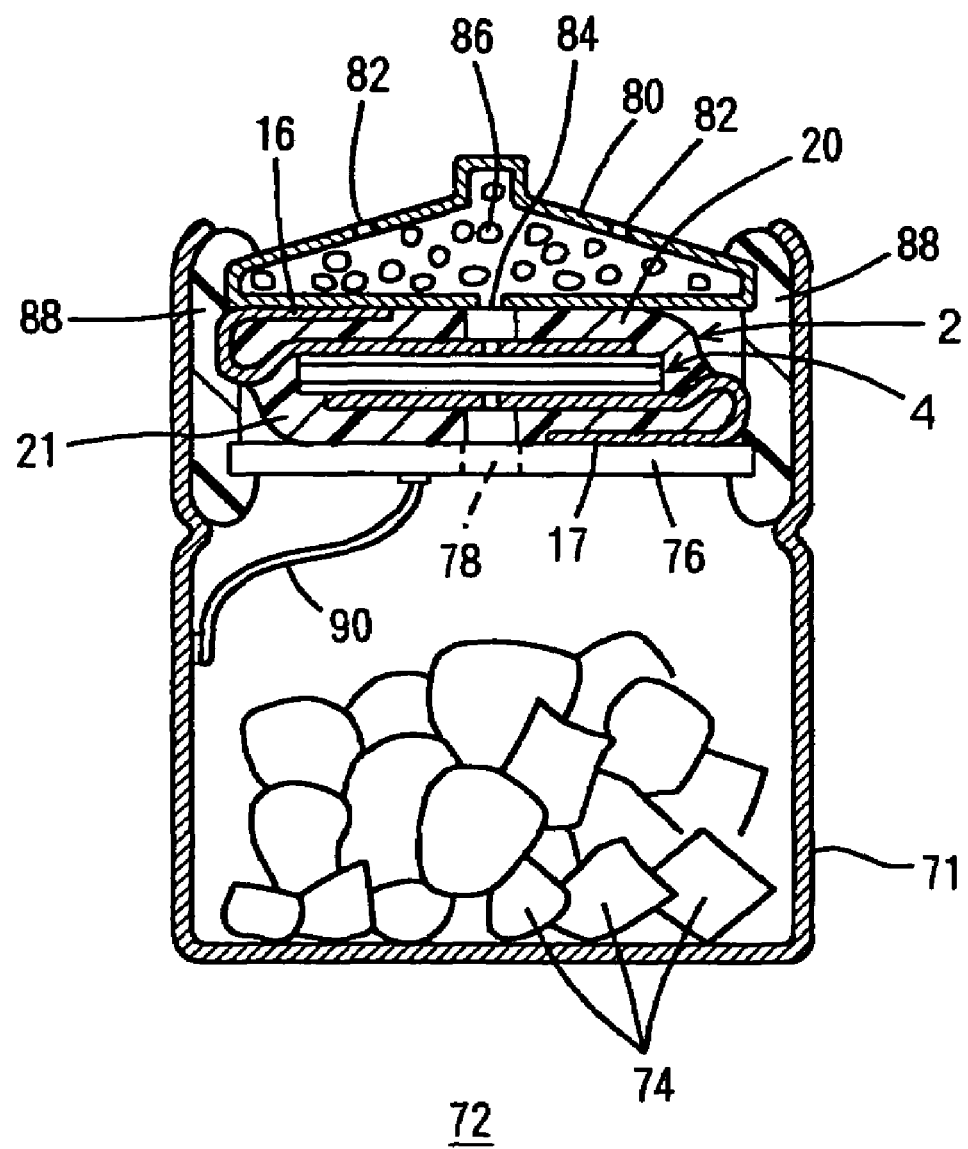
FIG. 7 is a sectional view of the gas sensor of a modification of the present invention.

This sensor unit 2 is not necessarily used in combination with the water pack 53. A gas sensor 72 which is combined with a metal can 71 is shown in FIG. 7. 74 denotes gelled water. The gelled water is produced by gelling water with a gelatinizer such as polyvinylamine, polyacrylamide, agar or gelatine. To prevent contamination of the MEA, it is desired that the gelled water does not contain any metal ions, such as sodium. The quantity of the gelled water 74 is, for example, about 5 to 10 g.

Deionized water or the like is used to prepare the gelled water. Deionized water, however, contains organic materials in many cases even if it does not contain cations or anions. If washing of the metal can 71 is not sufficient or if washing of the water pack 53 in the embodiment shown in FIG. 5 and FIG. 6 is defective, organic materials may enter into the gelled water. When organic materials are present in the gelled water or liquid water, molds grow in many cases. If the molds reach the counter electrode, the activity of the counter electrode is reduced. And if the molds enter the opening 19 in the metal plate 15, the molds may block the opening 19. Hence, it is desirable to add an antiseptic to the gelled water or liquid water to prevent molds growth. 1 to 30 weight %, for example, 10 weight % of an antiseptic such as glycerin, pentanol or ethylene glycol may be added to 100 weight % of water. Addition of a saturated aqueous solution of silver nitrate, about $1/1000$ in volume, to water will also produce an antiseptic effect.

76 denotes a metal washer, and 78 is an opening made in it. 80 denotes a cap made of a metal, and 82 is an opening made in an upper side face of the cap 80. 84 denotes an opening made in the bottom, at the center, of the cap 80, and is connected to the opening 24 of the sensor unit 2. 86 denotes active carbon contained in the cap 80. It is an example of the filtering material, and silica gel or the like may be used as the filtering material. 88 denotes an insulating gasket, which presses the cap 80 and the washer 76 in a direction to bring them closer to each other. The lead parts 16, 17 are bent, for example, in a way shown in FIG. 7, to make the lead part 16 contact the bottom of the cap 80 and to make the lead part 17 contact the metal washer 76. Under this condition, when they are pressed by the gasket 88, a contact between the cap 80 and the lead part 16 are secured, and a contact between the lead part 17 and the washer 76 are secured.

90 denotes a metal ribbon, which is used to electrically connect the washer 76 and the metal can 71. As a result, as shown in FIG. 7. the cap 80 is connected to the sensing electrode, and the metal can 71 is connected to the counter electrode. In the case of FIG. 7, a gas such as CO may bypass to the counter electrode side when the gas diffuses through a gap between the heat pressable film 20 and the cap 80 and diffuses again through a gap between the washer 76 and the heat pressable film 21. Such gaps are hardly generated because of the pressing by the gasket 88.

FIG. 8 shows the gas sensor of an example of comparison. The gas sensor 92 of FIG. 8 is similar to the gas sensor 72 of FIG. 7 except for that the MEA 6 being sandwiched between carbon sheets 12, 13 is used in place of the sensor unit 2 and this MEA 6 with carbon sheets 12, 13 is arranged between the washer 76 and the cap 80. In the gas sensor 92 of FIG. 8, there is an open space outside the carbon sheets 12, 13, and there is a possibility that the gas that has entered through the opening 84 into the carbon sheet 12 bypasses via this open space to the counter electrode side of the MEA 6. Hence, to examine the effect of bypassing via the open space outside the MEA 6, the gas sensor 92 of FIG. 8 was produced.

As explained in relation to FIG. 1 through FIG. 4, a proton conductive membrane Gore Select (Gore Select is a trade name of Japan Gore Tex), which was about 40 μm in thickness, was treated with a 5% Nafion-IPA solution. The treated membrane was covered, from above and below, by electrode membranes (thickness: 100 μm), which were porous Teflon sheets containing platinum-supporting carbon black. They were heat-pressed at 130° C., $1 \times 10^6$ Pa to form the MEA 6. The MEA 6 was cut into a disk of about 10 mm in diameter, and the disk was sandwiched between carbon sheets 12, 13, which were 200 μm in thickness. Then, they were sandwiched between a pair of metal plates, each of which had an opening of about 0.1 mm in diameter. They were sandwiched, from below and above, between polypropylene films of about 100 μm in thickness, and the whole assembly was heat-pressed at about 100 to produce the sensor unit 2. This gas sensor was heat-pressed onto the water pack to produce the embodiment.

A similar MEA 6 was sandwiched between similar carbon sheets 12, 13 to produce the gas sensor 92 having the structure shown in FIG. 8. In both cases, no gelled water 74 was filled.

Figure 9:
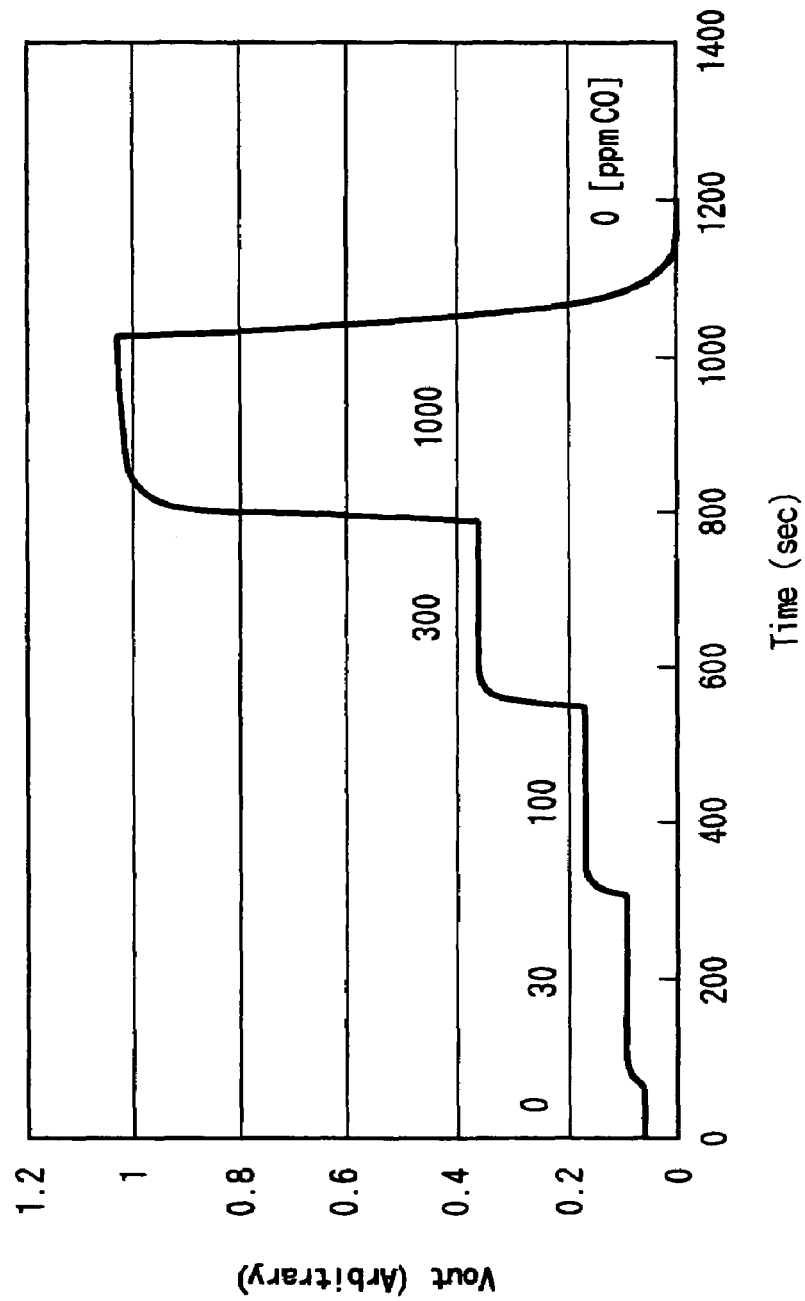
FIG. 9 is a waveform chart showing responses of the gas sensor of the embodiment at 30-1000 ppm of CO.
Figure 10:
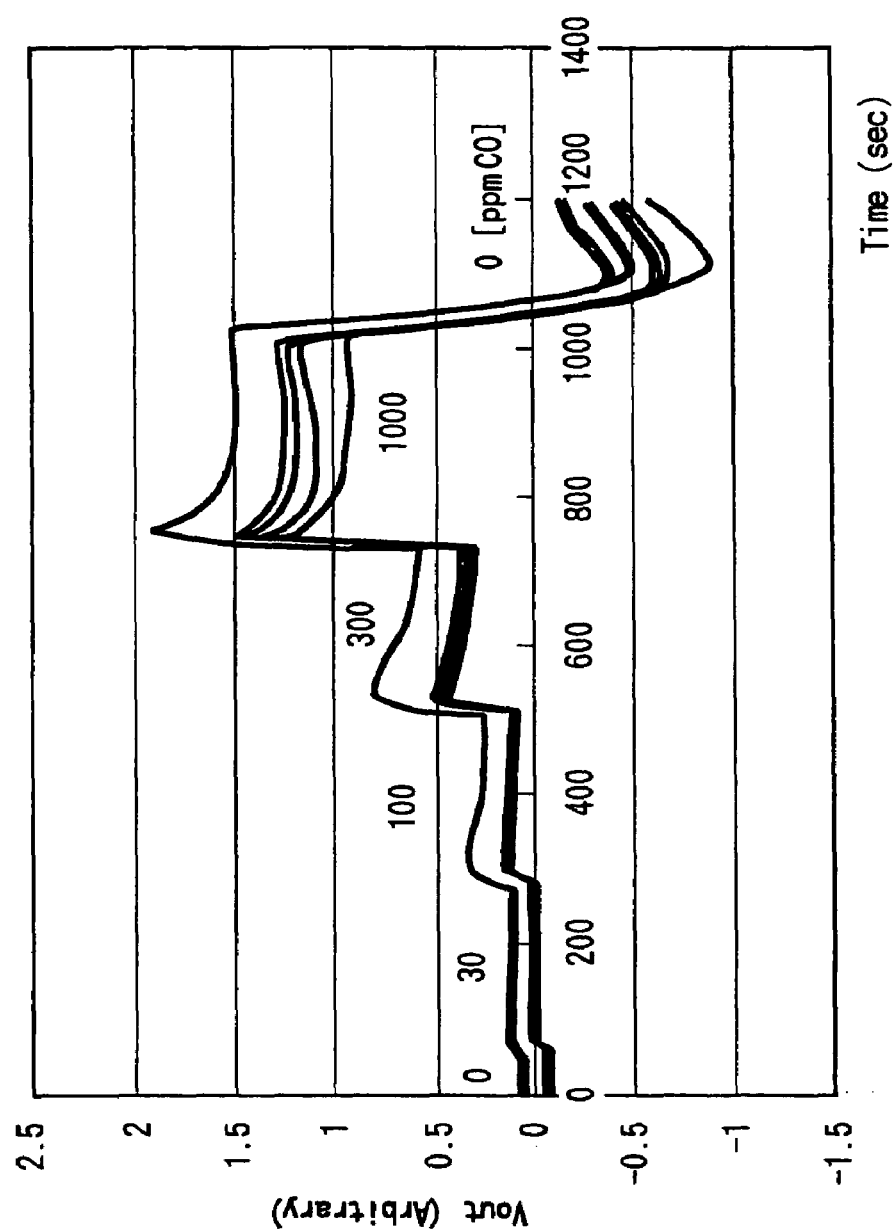
FIG. 10 is a waveform chart showing responses of the gas sensor of FIG. 8 at 30-1000 ppm of CO.

Response waveforms of these gas sensors at 30 to 1000 ppm of CO are shown in FIG. 9 and FIG. 10. The CO concentration was 0 ppm at the beginning and at the end. The concentration was changed to 30 ppm, 100 ppm, 300 ppm and 1000 ppm in between. The sensing electrode and the counter electrode of the sensor were short-circuited with a load resistance of about 100Ω, and the output to the load resistance was amplified. The amplified output was taken on the ordinate. The unit is arbitrary. FIG. 9 shows the characteristics of the gas sensor of FIG. 5, and FIG. 10 shows the characteristics of the gas sensor of FIG. 8, respectively. As can be seen clearly in the charts, the results of FIG. 10, of the sensor using no heat pressable films, indicate significant overshoots and significant undershoots.

The embodiment is a gas sensor having two electrodes; a sensing electrode and a counter electrode, but, for example, a gas sensor having three electrodes may be produced. In that case, two layers of the proton conductive membrane are provided in the MEA, and the metal plate is arranged between these two layers. Or the counter electrode of the embodiment may be divided into two parts, and one part may be used as a counter electrode and the other as a reference electrode.

Best Embodiment

FIG. 11 through FIG. 20 show the best embodiment of the present invention and its modifications. The best embodiment is similar to the embodiment of FIG. 1 through FIG. 10 except some specified points. The respective parts are similar to those of the embodiment of FIG. 1 through FIG. 10 if not specified otherwise.

In a proton conductor gas sensor 100 of FIG. 11 through FIG. 14, 102 denotes a sensor unit, 104 a bottle made of a synthetic resin, and 106 a cap, which is airtightly screwed on the bottle 104. The bottle 104 is formed by two layers; a first resin 108 and a second resin 109. The first resin 108 uses a fine resin of which air permeability is extremely low, such as zeonor (trade name of Japan Zeon). Zeonor comprises polyethylenenaphthalate (PEN), poval or cyclic olefin polymer. For the second resin 109, an inexpensive commodity plastic such as polypropylene (PP) or polyethylene (PE) is used. The use of the first resin 108 of low air permeability is to reduce the air permeability of the bottle 104 and effectively utilize the water contained in the bottle 104.

110 is an inner bag made of a film of an appropriate synthetic resin such as polyethylene or polypropylene. The inner bag 110 is watertight, yet is permeable to water vapor, and gradually releases water contained in it. 111 denotes a cushion made of foamed polystyrene or the like. The cushion 111 prevents movement and eventual breakage of the inner bag 110 in case of a fall of the gas sensor 100 or a similar event. The inner bag 110 and the cushion 111 may be omitted, and water may be stored as liquid water, gelled water, etc. Further, it is desired that glycerin or the like is added to prevent mold growth in the water contained in the inner bag 110.

112 denotes a thread groove provided in the cap 106. The thread groove 112 fits with a corresponding external thread provided in the bottle 104 to prevent water vapor from escaping through a gap between the cap 106 and the bottle 104. 114 is an opening that is provided in the top of the cap 106. The sensor unit 102 is mounted on the top of the cap 106 with an adhesive or the like, and the opening 114 is made to connect to the opening 25 provided in the heat pressable film 21 and the opening provided in the second metal plate.

Figure 13:
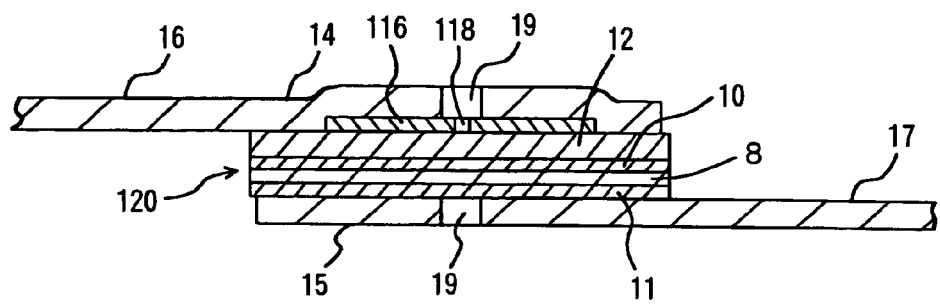
FIG. 13 is an enlarged sectional view showing the MEA and the lead parts in the best embodiment.

As shown in FIG. 13, in the best embodiment, the proton conductive membrane 8 of the MEA 120 is, for example, about 20 μm in thickness, and the sensing electrode 10 and the counter electrode 11 are about 10 μm in thickness, respectively. The carbon sheet 12 is hydrophobic and is, for example, about 80 μm in thickness. The carbon sheet 12 evenly distributes the external atmosphere, which is introduced through the openings 19, 118, over the entire face of the sensing electrode 10. On the counter electrode 11 side, the carbon sheet may be provided or eliminated.

The metal plates 14, 15 are stainless steel plates of, for example, 0.25 mm in thickness, and the openings 19, 19 are about 0.2 mm in diameter. 116 denotes a stainless steel film, and here a stainless steel film of 100 μm in thickness is used. An opening 118 of 100 μm in diameter is made in the film 116 to connect to the opening 19. As the stainless steel film 116 is thin and can be easily pressed, the opening 118 can be easily made by pressing or the like to have a desired diameter. The film 116 may be a metal other than stainless steel. In the embodiment, as the gas sensor 100 is used under diffusion control, the supply rate of CO or the like to be detected through the opening 118 determines the sensor output. Hence, when the diameter of the opening 118 can be made constant, the dispersion of the sensor output can be reduced.

Figure 14:
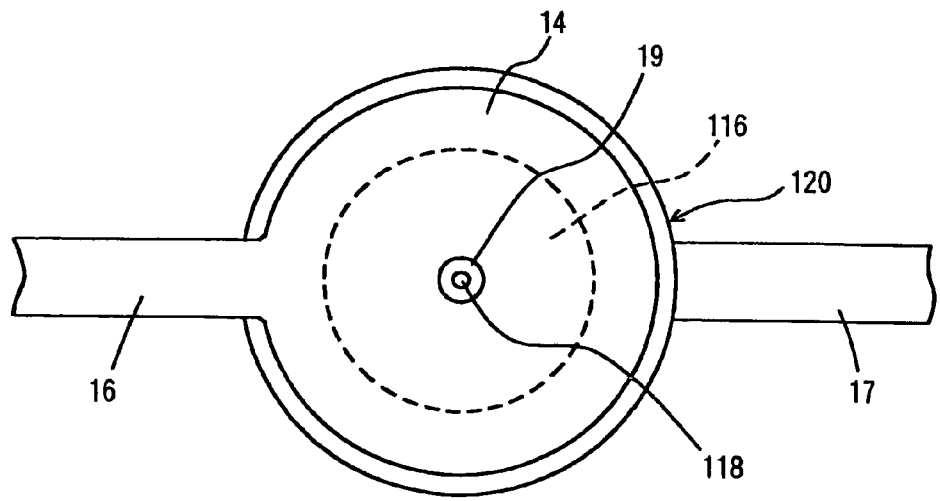
FIG. 14 is an enlarged plan view of the MEA with lead parts in the best embodiment.
Figure 15:
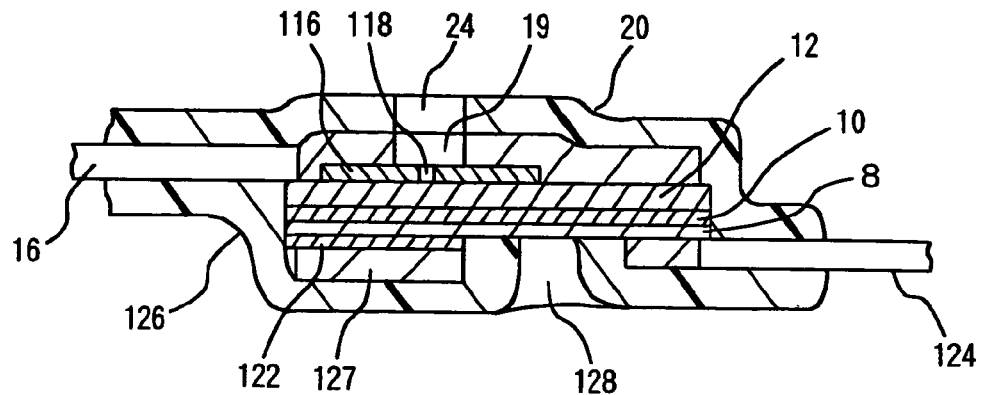
FIG. 15 is an enlarged sectional view of the sensor unit of a modification of the best embodiment.
Figure 16:
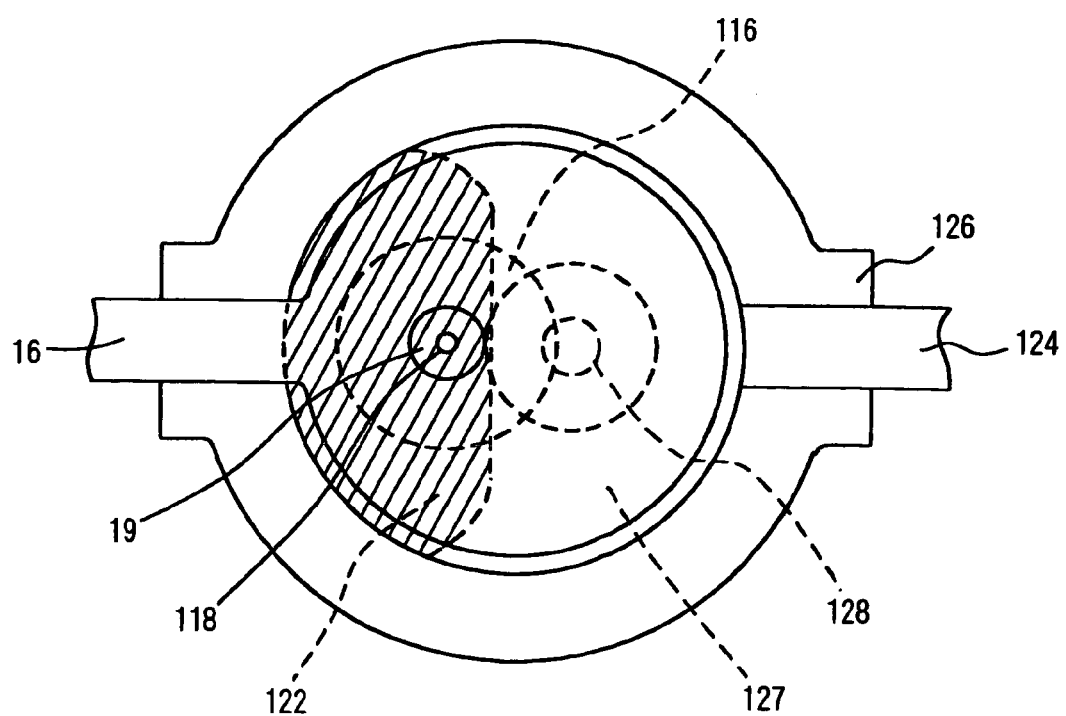
FIG. 16 is a plan view of the sensor unit of FIG. 15. The upper heat pressable film is not shown.

FIG. 14 shows the MEA 120 seen from the side of the metal plate 14. FIG. 15 and FIG. 16 show a modification of the MEA, wherein the counter electrode 122 is provided to cover about one half rather than the entirety of the proton conductive membrane 8. The remaining half surface of the proton conductive membrane 8 is made to contact liquid water or water vapor through the opening 128. It should be noted that the surface of the proton conductive membrane 8 has a property of repelling liquid water. As for the metal plate 127 having the lead part 124, a hole is provided in a part corresponding to the opening 128, and the exposed surface of the proton conductive membrane 8 is allowed to contact liquid water or water vapor through this hole. To correspond to the shift of the counter electrode 122 away from the center of the proton conductive membrane 8, the positions of the openings 118, 19, 24 are shifted. 126 is a heat pressable film on the metal plate 127 side, and here the heat pressable film 126 covers the edge of the metal plate 127 around the opening 128, but the edge of the metal plate 127 may be exposed around the opening 128.

When a combination of a bottle 104 and a cap 106 is used, the cap can be removed from the bottle 104 to replace or replenish water in the bottle 104. In the embodiment, as an inner bag 110 and cushions 111 are used, cushions 111 are taken out first, then the inner bag 111 holding depleted water is taken out and replaced by a new inner bag. Then the cushions are packed again and the cap 106 is screwed on.

Figure 17:
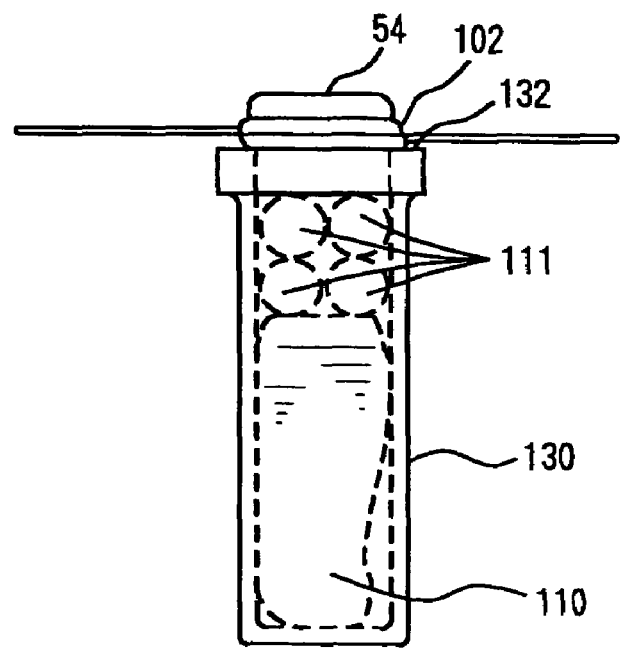
FIG. 17 is a side view showing a modification of the water container in the best embodiment.

As shown in FIG. 17, a tube 130 with a bottom may be used as a water container. A flange 132 is provided at the top of the tube 130, and a sensor unit 102 may be attached to a flat portion of the top face of the flange 132 with, for example, an adhesive or the like. The interface between the sensor unit 102 and the flange 132 is kept airtight in this case as well so as to prevent depletion of water. Moreover, it is also desirable that the tube 130 is formed by a first resin 108 and a second resin 109 to prevent water vapor from escaping.

Figure 11:
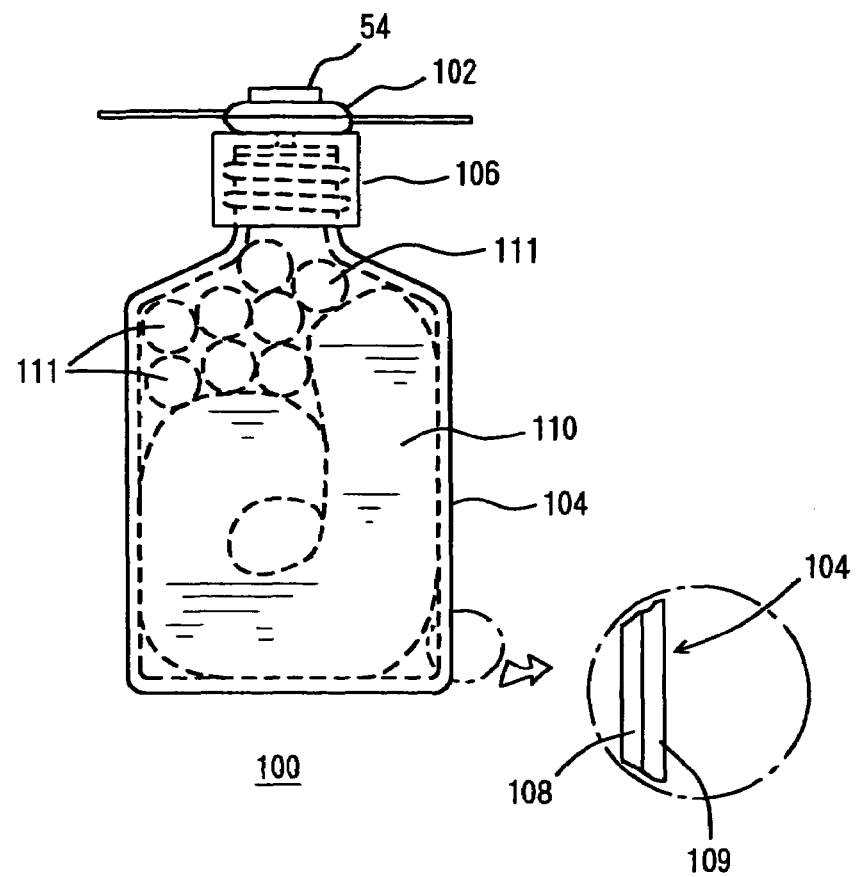
FIG. 11 is a side view of the gas sensor of the best embodiment of the present invention.
Figure 12:
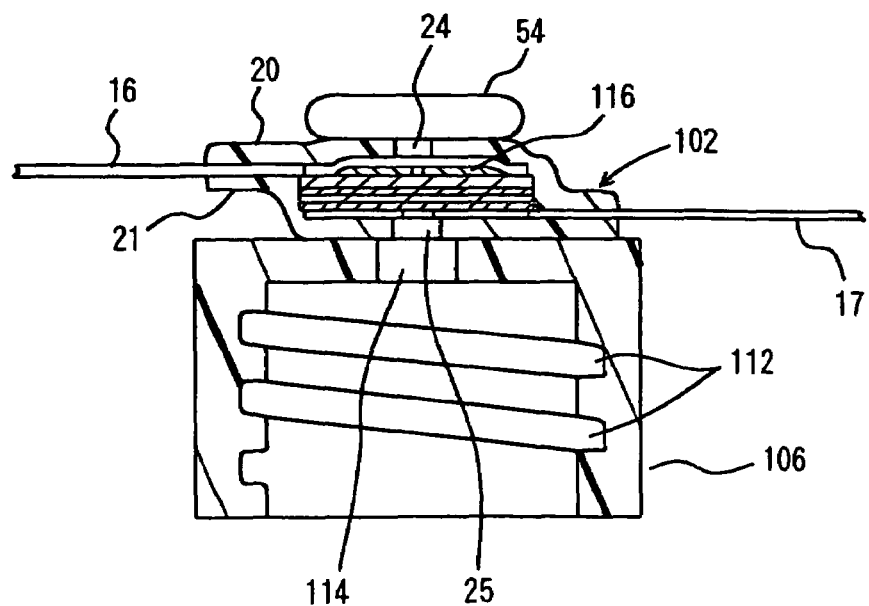
FIG. 12 is an enlarged sectional view of the cap part of the gas sensor of the best embodiment.
Figure 18:
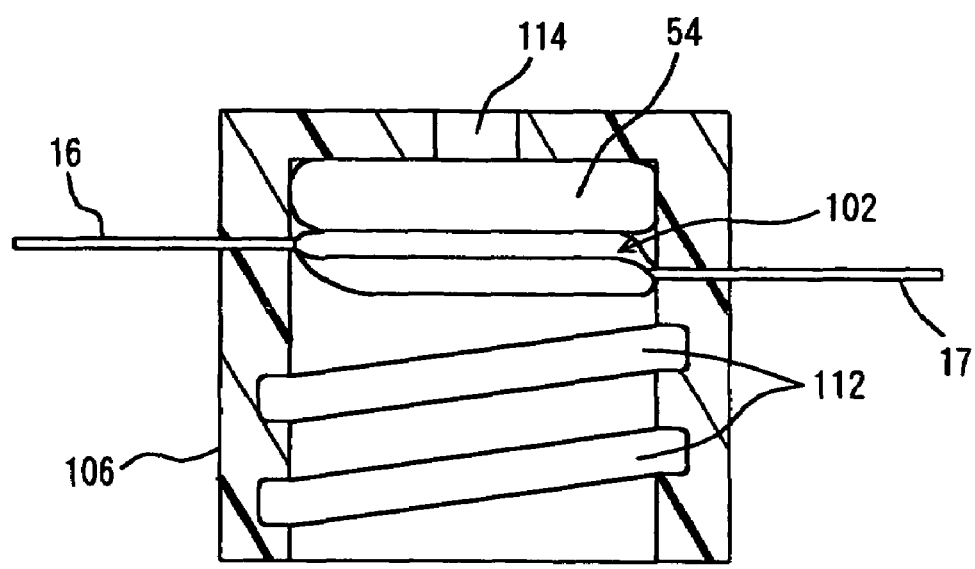
FIG. 18 is a sectional view showing a modification of fitting of the filter and the sensor unit onto the cap in the best embodiment.

In FIG. 11 and FIG. 12, the filter 54 and the sensor unit 102 are provided on the outer face of the top of the cap 106. In contrast to this, as shown in FIG. 18, the sensor unit 102, or the sensor unit 102 and the filter 54 may be fitted on the inside of the cap 106. With this arrangement, as the filter 54 is required to have, for example, hydrophobicity, it is desirable that the filer 54 is entirely covered by a watertight membrane such as a polyethylene film.

Figure 19:
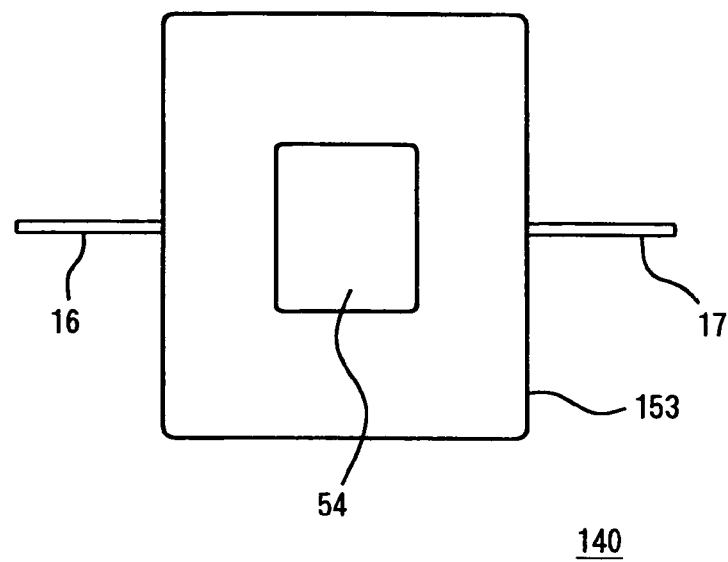
FIG. 19 is a plan view showing a modification of the best embodiment wherein the sensor unit is stored in a water pack.
Figure 20:
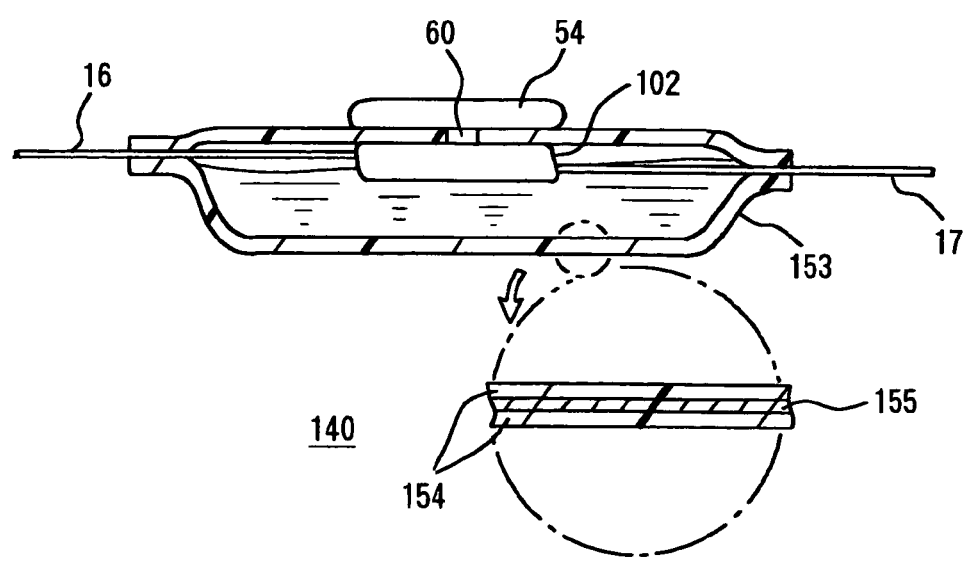
FIG. 20 is an enlarged sectional view of FIG. 19.

FIG. 19 and FIG. 20 show a gas sensor 140, which uses a flexible water pack 153. The sensor unit 102 is one that is used in the best embodiment. The water pack 153 comprises a pair of films 154, 154 of resin, for example, polypropylene, and a water vapor tight film 155, which is sandwiched between the pair of films 154, 154. The water vapor tight film 155 is also a airtight film. As for the material of the film 155, a ceramic thin film (1 μm or smaller in thickness) of silica, alumina, etc. is used, and this ceramic film is formed on one resin film 154 by vapor deposition or the like. If a metal film is used for the water vapor tight film 155, the edge of the metal film will be exposed around an opening that is provided to guide water vapor to the sensor unit 2, and this part is wetted with water and oxidized, and in turn, water vapor will be depleted more quickly in some cases. In contrast to it, a ceramic water vapor tight film does not deteriorate even if it is wetted with water. Thus the life of the water pack 153 can be extended.

Figure 23:
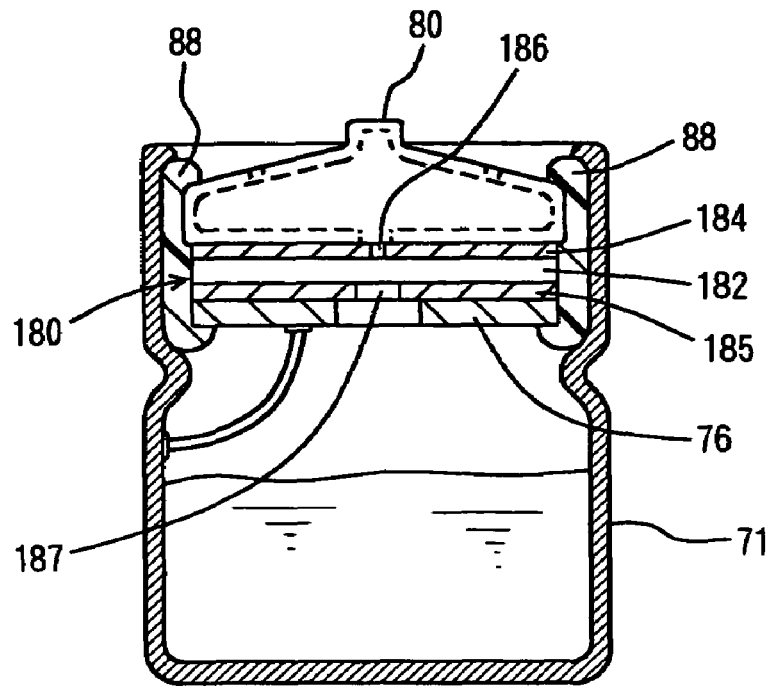
FIG. 23 is a sectional view of the sensor of the example for comparison.

FIG. 21 through FIG. 23 show the benefits of providing the stainless steel film 116. FIG. 21 shows the output distribution of the gas sensor of the best embodiment of FIG. 11 at 1000 ppm of CO. The number of the sensors used was 120. Here the stainless steel film 116 of 0.1 mm in thickness was used, and the opening 118 of 0.1 mm in diameter was made in the film 116 by pressing. FIG. 22 shows the output distribution of the gas sensor of the example for comparison shown in FIG. 23. The number of the sensors used was 480, and the diagram shows the outputs at 1000 ppm of CO. In FIG. 23, 180 denotes the sensing element, and 182 denotes its assembly, which comprises the MEA 120 (FIG. 13) and two carbon sheets that are layered on the MEA 120 from above and below. 184 and 185 are metal plates. They are stainless steel plates of 0.25 mm in thickness. The metal plate 184 on the sensing electrode side is provided with an opening of 0.1 mm in diameter by etching. The metal plate 185 on the counter electrode side is provided with an opening 187 of 0.2 mm in diameter by press punching. The reason of making the opening 186 of 0.1 mm in diameter in the metal plate on the sensing electrode side by etching is that the plate thickness of the metal plate is greater than the diameter of the opening and it is difficult to punch. Then a gasket 88 is used, and the upper edge of the metal can 71 is caulked to clamp the sensing element 180 between the washer 76 and the cap 80.

Comparison of FIG. 21 and FIG. 22 shows that the example for comparison of FIG. 22 had a wider distribution of the sensor outputs. This indicates that the diffusion control on the sensing element is difficult in the case of FIG. 22, and in turn, that when the opening diameter is controlled by etching, the dispersion of the opening diameter is large. Moreover, in FIG. 22, there is an abnormal peak at about 3 V of output. It may be presumed that at the time of caulking the pressure from the cap 80 onto the sensing element 180 is uneven and the carbon sheets are displaced.

Figure 24:
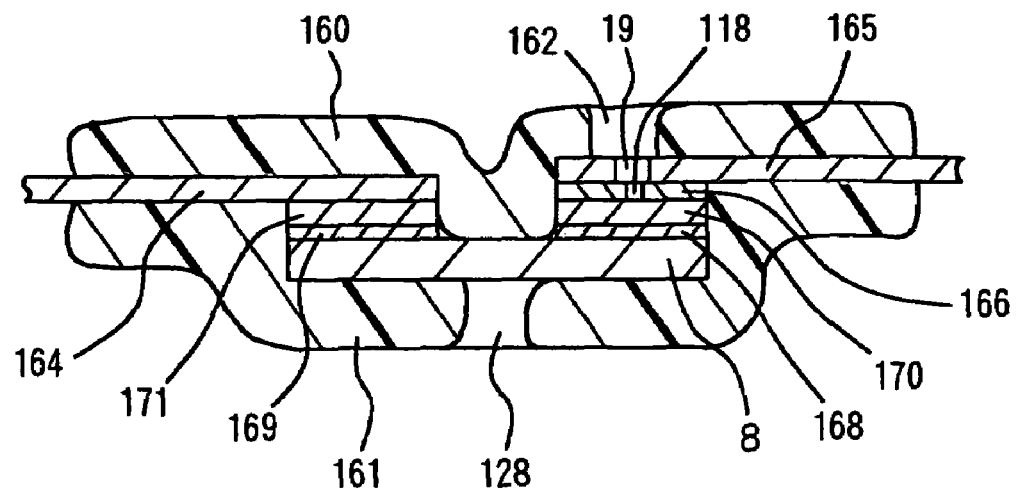
FIG. 24 is a sectional view showing a modification of the sensor unit in the best embodiment.
Figure 25:
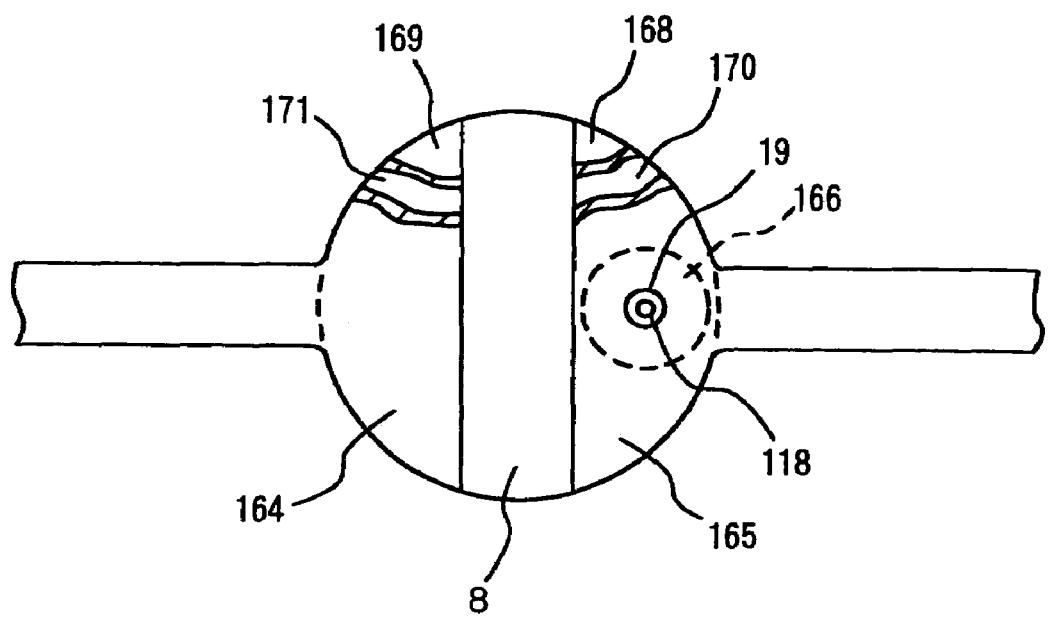
FIG. 25 is a partially-cut-away plan view of the sensor unit of the modification of FIG. 24.
Figure 26:
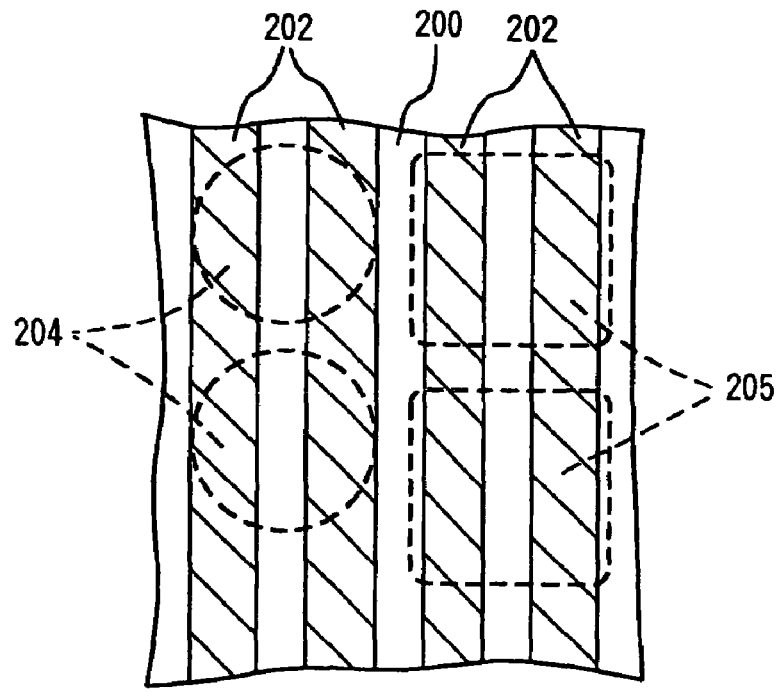
FIG. 26 is a diagram showing cutting the MEA out of a proton conductive membrane with electrode pattern.

FIG. 24 through FIG. 26 show a modification of the sensor unit of the best embodiment. In FIG. 24, 160 and 161 denote heat pressable films, and 162 denotes an opening made in the heat pressable film 160, and the heat pressable film 161 has an opening 128. 8 is the proton conductive membrane, a sensing electrode 168 and a counter electrode 169 are provided on the same face of the proton conductive membrane 8, and the heat pressable film 160 adheres closely to the proton conductive membrane 8 in the gap between the sensing electrode 168 and the counter electrode 169. 164, 165 are metal plates of stainless steel or the like of 0.25 mm in thickness. The metal plate 165 on the sensing electrode side is provided with an opening 19 of, for example, 0.2 mm in diameter. A stainless film 166 of, for example, 0.1 mm in thickness is provided with an opening 118 of, for example, 0.1 mm in diameter. 170 and 171 denote carbon sheets, and they may be omitted.

In the case of FIG. 24, the gas of CO, etc. to which diffusion control is given by the opening 118 is distributed by the carbon sheet 170 over the entire face of the sensing electrode 168, and reacts, at the sensing electrode 168, with water vapor, which is supplied from a water container such as the bottle 104 (FIG. 13) through the opening 128 to the proton conductive membrane 8. Proton which is generated at the sensing electrode 168 diffuses in the proton conductive membrane 8 to the counter electrode 169 side and reacts, at the counter electrode 169, with oxygen in air that is confined in the carbon sheet 171 at the time of production to change into water vapor. The required oxygen at the counter electrode is supplied, in addition to the oxygen in air that is confined in the carbon sheet 171 at the time of its production, by the slight oxygen permeability of the heat pressable film 160 and the proton conductive membrane 8, and through a minute gap between the heat pressable film 160 and the proton conductive membrane 8.

FIG. 25 shows the sensor unit of FIG. 24, from which the heat pressable films 160, 161 are removed. The pair of metal plates 164, 165 are arranged on the same face in relation to the proton conductive membrane 8, the diffusion control to the counter electrode is given by the opening 118, and the proton that is generated at the sensing electrode will diffuse from the right towards the left in FIG. 25 and reach the counter electrode. As the sensing electrode 168 is subjected to diffusion control by the opening 118, the oxygen consumption at the counter electrode 169 is very small, and the sensor unit can function with the oxygen that is supplied at a very low rate from the air confined in the carbon sheet 171 at the time of its production and through the heat pressable films 160, 161, etc.

FIG. 26 shows the production process of the MEA, which was used in the modification of FIG. 24 and FIG. 25. 200 denotes a proton conductive membrane on which electrodes 202 are provided, for example, in stripes. Circular or rectangular pieces are punched out of the proton conductive membrane to produce the MEAs 204, 205, etc.

In the embodiments, a pair of metal plates and an MEA are arranged inside a pair of heat pressable films, and the electrical connections between the metal plates and the MEA are secured by the shrinking forces of the heat pressable films. As the assembly of the sensor unit is free of any process of exerting a large impact, the metal plates and carbon sheets will not be displaced in relation to the electrodes. This, in turn, reduces dispersion of the sensor output. Moreover, in place of accurately making an opening of a desired size in a metal plate, an opening is made in a thin stainless steel film. This reduces dispersion of the opening diameter, and in turn, reduces dispersion of the sensor output. When a water container comprising a bottle and a cap is used, water can be replaced and the life of the sensor can be extended. Furthermore, by selecting the materials of the bottle and the water pack, water vapor can be prevented from escaping and the life of the sensor can be extended. When an inner bag and cushions are used, water will not leak out irrespective of the position the sensor may take. When cushions are used, the inner bag will not break in case of dropping of the sensor. When the sensor unit is stored inside the water pack or the bottle, the sensor unit will not be damaged during transportation or in service.

The invention claimed is:

1. A proton conductor gas sensor having a sensor unit comprising
    a sensing element (4) comprising
    a proton conductive membrane (8);
    a membranal sensing electrode (10) and a membranal counter electrode (11) being separated from each other and attached at least on one face of the proton conductive membrane (8);
    a first metal plate (14) covering the sensing electrode and being provided with an opening (18), and
    a second metal plate (15) covering the counter electrode being characterized in that the first metal plate (14) is provided with a lead part (16), that the second metal plate is provided with a lead part (17),
    that said sensor unit additionally comprises a first synthetic resin film (20) having a thickness of 30 μm to 200 μm, and a second synthetic resin film (21) having a thickness of 30 μm to 200 μm, sandwiching the sensing element (4) between themselves and being greater in size than any of the proton conductive membrane (8), the sensing electrode (10), the counter electrode (11), the first and the second metal plates (14,15),
    that the first and second synthetic resin films (20,21) are bonded together, and by that, the first metal plate (14) is pressed towards the sensing electrode side and the second metal plate (15) is pressed towards the counter electrode side, and an electric contact between the first metal plate (14) and the sensing electrode (10) and an electric contact between the second metal plate (15) and the counter electrode (11) are secured, and
    that the respective lead parts protrude from and between the first and the second synthetic resin films outwards.

2. A proton conductor gas sensor as recited in claim 1, being characterized in that
    the first synthetic resin film is provided to cover the first metal plate, and that
    a filter for removing poisoning substances is provided between the first metal plate and the first synthetic resin film or outside the first synthetic resin film.

3. A proton conductor gas sensor as recited in claim 1, being characterized in that
    the first synthetic resin film is provide to cover the first metal plate,
    that the sensor unit is mounted at a flexible pack on the side of the second synthetic resin, wherein the flexible pack is covered by an airtight film, holds water in a condensed phase, and is provided with a part where the airtight firm is cut away, and
    that the part is connected to the second synthetic resin film.

4. A proton conductor gas sensor as recited in claim 3, being characterized in that the water in a condensed phase is made to contain an antiseptic.

5. A proton conductor gas sensor as recited in claim 3, being characterized in that the flexible pack comprises at least two layers of synthetic resin films and an airtight ceramic film being sandwiched between the two layers.

6. A proton conductor gas sensor as recited in claim 3, being characterized in that the sensor unit is mounted inside the flexible pack.

7. A proton conductor gas sensor as recited in claim 1, further comprising a third metal plate being thinner than the first metal plate, being connected to the opening in the first metal plate, and being provided with an opening being smaller in diameter than that in the first metal plate.

8. A proton conductor gas sensor as recited in claim 1, being characterized in that
    the first synthetic resin film is provided to cover the first metal plate, and that
    the sensor unit is mounted on a water container of a synthetic resin on the side of the second synthetic resin film.

9. A proton conductor gas sensor as recited in claim 8, being characterized in that
    the water container comprises a synthetic resin bottle containing a volume of water in a condensed phase, and a synthetic resin cap being airtightly screwed on the bottle and having an opening in a position opposite to the bottle, and that
    the sensor unit is mounted at the cap in the opposite position.

10. A proton conductor gas sensor as being recited in claim 9, being characterized in that the sensor unit is mounted inside the cap at the opposite position.

11. A proton conductor gas sensor as recited in claim 8, being characterized in that the water in a condensed phase is contained in a watertight and water vapor permeable inner bag, and the inner bag is contained in the water container.

* * * * *